United States Patent [19]

Sundermann et al.

[11] 4,154,752

[45] May 15, 1979

[54] PREPARATION OF PARTIALLY CARBODIIMIDIZED METHYLENEBIS (PHENYL ISOCYANATE)

[75] Inventors: Rudolf Sundermann, New Martinsville; William E. Slack, Moundsville, both of W. Va.

[73] Assignee: Mobay Chemical Corporation, Pittsburgh, Pa.

[21] Appl. No.: 903,308

[22] Filed: May 5, 1978

[51] Int. Cl.$^2$ ........................................ C07C 119/055
[52] U.S. Cl. ........................ 260/453 SP; 260/239 A; 260/453 AM
[58] Field of Search ................ 528/901; 260/453 AM, 260/453 SP

[56] References Cited

U.S. PATENT DOCUMENTS

| | | | |
|---|---|---|---|
| 3,152,162 | 10/1964 | Fischer et al. | 260/453 AR |
| 3,761,502 | 9/1973 | Kan et al. | 260/453 P |
| 4,014,935 | 3/1977 | Ibbotson | 260/566 R |
| 4,088,665 | 5/1978 | Findeisen et al. | 260/453 AM |

*Primary Examiner*—Dolph H. Torrence
*Attorney, Agent, or Firm*—Gene Harsh; Joseph C. Gil

[57] ABSTRACT

The instant invention is directed to storage stable liquid, partially carbodiimidized methylenebis(phenyl isocyanate) and to the method of manufacture thereof. The products of the instant invention are produced by heating methylenebis(phenyl isocyanate) at a temperature of from 150° to 300° C. in the presence of from 1 ppb to 10 ppm of a phospholine oxide catalyst. The reaction mixture is then cooled once the desired isocyanate content has been reached. The resultant product can be used to produce a variety of isocyanate-addition reaction products, including polyurethanes, polyureas and the like.

6 Claims, No Drawings

PREPARATION OF PARTIALLY CARBODIIMIDIZED METHYLENEBIS (PHENYL ISOCYANATE)

BACKGROUND OF THE INVENTION

Methylenebis(phenyl isocyanate) is commonly used in the production of cellular and non-cellular polyurethanes. Substantially pure methylenebis(phenyl isocyanate) [i.e., methylenebis(phenyl isocyanate) containing less than 5% by weight of polyisocyanate of functionally greater than 2, and including 4,4'-methylenebis(phenyl isocyanate), 2,4'-methylenebis(phenyl isocyanate), and mixtures thereof] is normally solid at room temperature. In general, the substantially pure material must be heated to a liquid state and must be maintained at the heated temperature during processing. Thus, the art has looked to a variety of means of producing modified methylenebis(phenyl isocyanate) which are liquid and storage stable.

One approach suggested in the art has been to heat the substantially pure methylenebis(phenyl isocyanate) in the presence of a trialkyl phosphate to produce a liquid, partially carbodiimidized isocyanate product. See, e.g., U.S. Pat. Nos. 3,384,653 and 3,449,256.

It has also been proposed that heating methylenebis(phenyl isocyanate) alone, in the absence of any catalyst, produced a partially carbodiimidized isocyanate which crystallizes upon standing. See, e.g., U.S. Pat. No. 3,152,162. It is believed that this is due to the uncontrolled reaction occurring during the heating step.

Finally, it has been proposed to form liquid, partially carbodiimidized isocyanates by using phospholine oxide catalysts in combination with catalyst poisons. In one embodiment, the isocyanate is heated to below 150° C. in the presence of from 1 to 10 ppm of phospholine oxide. The reaction is then terminated by addition of one or more of the halides of hydrogen, phosphorous, or tin, or an oxyhalide of phosphorous or sulphur. See, e.g., U.S. Pat. No. 4,014,935. In yet another proposal, the isocyanate is mixed with from 0.1 to 100 ppm of a phospholine oxide at a temperature of from 0° to 200° C., and the reaction is then terminated by addition of a catalyst poison. See, e.g., U.S. application Ser. No. 715,092, filed on Aug. 17, 1976 now U.S. Pat. No. 4,088,665.

DESCRIPTION OF THE INVENTION

It has now been found that liquid, storage stable, partially carbodiimidized methylenebis(phenyl isocyanates) can be produced by heating the isocyanate to a temperature of from 150° to 300° C. in the presence of from 1 ppb (parts per billion) to 10 ppm (parts per million) of a phospholine oxide, and thereafter terminating the reaction by cooling the reaction mixture to 100° C. or less.

Useful phospholine oxides are known and are generally of the formulae:

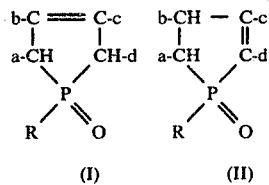

(I)        (II)

wherein R represents a lower alkyl radical, (generally of 1 to 4 carbon atoms), a phenyl radical, an alkoxy radical, (generally of 1 to 4 carbon atoms), a hydrogen atom or an alkenyl radical (generally of 2 to 4 carbon atoms); a, b, c and d each represent hydrogen, a halogen atom, a lower alkyl (generally of 1 to 4 carbon atoms), a lower alkenyl (generally of 2 to 4 carbon atoms) phenyl, a cyclohexyl or a polymethylene group which together with two neighboring C-atoms of the heterocyclic ring forms a cycloaliphatic ring.

In the process according to the invention, the isocyanate to be partially carbodiimized is mixed with the carbodiimidization catalyst at temperatures of from about 150° to about 300°, and preferably at 180° to 240° C., and most preferably at 190° to 210° C. The carbodiimidization reaction is conducted to the desired degree of carbodiimidization within the specified temperature ranges and upon reaching the desired degree of carbodiimidization the reaction is terminated by cooling the reaction mixture to 100° C. or lower.

The "degree of carbodiimidization" is herein defined as the percentage of isocyanate groups present in the starting isocyanate which are coverted into carbodiimide groups with the evolution of carbon dioxide by the process according to the invention. The degree of carbodiimidization can be determined during the process according to the invention by the quantity of carbon dioxide evolving from the reaction mixture. This volumetrically determinable carbon dioxide quantity thus provides information on the degree of carbodiimidization achieved at any time during the process of the invention. In the process of the invention, the carbodiimidization reaction is terminated on reaching a degree of carbodiimidization of from 1 to 90%, and preferably from 5 to 30%.

Carbodiimidization catalysts which are suitable for the process according to the invention are organic phosphorous compounds of the above formulae (I) and (II). These phosphorous compounds are known and can be produced by known processes (cf. G. M. Kosolapoff, L. Maier, Organic Phosphorous Compounds, Wiley-Interscience, New York, 1972 et seq. Vol. 3, pages 370 to 371, pages 458 to 463 and Vol. 4, pages 9 to 10, page 48). Such phospholine oxides are described in U.S. Pat. Nos. 2,663,737; 2,663,738; 2,663,739; 2,941,966 and 2,853,473, the disclosures of which are herein incorporated by reference. Specific examples of useful materials include 1-methyl-1-oxophospholine, 1-ethyl-1-oxo-phospholine, 1-butyl-1-oxophospholine, 1-(2-ethylhexyl)-1-oxophospholine, 1-methyl-1-thiophospholine, 1-(2-chloroethyl)-1-oxophospholine, 1-phenyl-1-oxophospholine, 1-p-tolyl-1-oxophospholine, 1-chloromethyl-1-oxophospholine, 1,3-dimethyl-1-oxophospholine, 1,2-dimethyl-1-oxophospholine, 1-methyl-3-chloro-1-oxophospholine, 1-methyl-3-bromo-1-oxophospholine, 1-chlorophenyl-1-oxophospholine, 1,3,4-trimethyl-1-oxophospholine, 1,2,4-trimethyl-1-oxophospholine, 1,2,2-trimethyl-1-oxophospholine, 1-phenyl-3-methyl-1-oxophospholine and 1-phenyl-2,3-dimethyl-1-oxophospholine.

These compounds generally have a double bond either in the 2,3 or in the 3,4 position. In general in the process according to the invention, phospholine oxides are used which are technical mixtures both of the 2,3 and the 3,4 unsaturated compounds.

Catalysts which are particularly preferred for use in the process according to the invention are those of the above specified formulae (I) and (II), in which R represents an unsubstituted alkyl radical having from 1 to 4 carbon atoms, an unsubstituted alkoxy radical having from 1 to 4 carbon atoms or a phenyl radical; a, b, c and d which are identical or different radicals represent hydrogen or an unsubstituted alkyl radical having from 1 to 4 carbon atoms.

To carry out the process according to the invention, 1 ppb to 10 ppm, and preferably from 0.05 to 5 ppm of the catalyst based on the isocyanate is introduced with stirring at a temperature of from 150° to 300° C., preferably 180° to 240° C., and most preferably 190° to 210° C., optionally under pressure, into the liquid or dissolved isocyanate. After reaching the desired degree of carbodiimidization, the reaction is terminated by cooling to 100° C. or less. Because of the extremely low concentration of catalysts used, it has been found some of the phosphorous compound may volatilize during the reaction. In such cases, it may be necessary to add more catalysts. However, even if added catalyst is necessary, in no event should the total amount of catalyst used during the reaction exceed the limits set forth above. If more than 10 ppm of catalyst are used, it has been found that the final product is not stable and will continue reacting even after cooling.

The process according to the invention may be carried out batchwise but is preferably carried out continuously. In the continuous process for preparing polyisocyanates which contain a carbodiimide-isocyanate adduct, the polyisocyanate is preferably passed through a continuous apparatus, such as, for example, a heated reaction tube or a heated reaction chamber, for example, a reaction tower, and the catalyst is continuously mixed with the polyisocyanate before the hot reaction zone is reached. The addition of catalyst may, however, also be carried out in the heated reaction chamber.

The degree of conversion of the isocyanate groups of the polyisocyanate into carbodiimide groups can be regulated by the rate of flow through the apparatus, that is, the time of residence in the reaction zone, the quantity of catalyst and the reaction temperature.

The reaction product is advantageously chilled to about temperatures of less than 100° C., preferably from about 20° C. to about 60° C., immediately after leaving the hot reaction zone. When the process is carried out continuously, this cooling can be achieved especailly easily by means of a heat exchanger. The sudden cooling instantaneously brings the formation of carbodiimide to a stop and the critical temperature regions in which, for example, the diisocyanates of diphenylmethane tend to form dimers, can be by-passed so that such unwanted side reactions do not occur. Carbodiimides add to isocyanates in the cold to form uretone imines so that polyisocyanates containing a carbodiimide-isocyanate adduct (polyisocyanates containing uretoneimine groups) are obtained by the process according to the invention.

A particular advantage of the process according to the invention is the fact that it permits the production of only partially carbodiimidized isocyanates in a particularly simple manner, the substances being distinguished by a particularly low content of foreign substance such as, e.g. deactivated catalyst.

The carbodiimides having isocyanate groups according to the invention or their solutions in carbodiimide-free polyisocyanates are valuable starting products for the diisocyanates-polyaddition process and can be used for the production of plastics varying from hard to elastic, optionally in cellular form, for the production of varnishes, coverings, coatings, films and molded bodies.

Polyurethanes produced in this way contain in the polymer molecule permanently incorporated carbodiimide groups or uretoneimine groups (=masked carbodiimide groups), which at the same time constitute anti-ageing agents against the hydrolysis of ester compounds and also reducing the inflammability of the plastics.

The following examples serve to illustrate the present invention. Unless otherwise indicated, quantities are given in parts by weight or percentages by weight. In the examples, the phospholine oxide used was an isomer mixture of 1-methyl-1-oxophospholine.

EXAMPLES

EXAMPLE 1

997 parts of 4,4'-diisocyanatodiphenylmethane were heated to 200° C. in a 1 liter 3 necked flask and mixed with 0.0173 parts of a 3% phospholine oxide solution in toluene (0.5 ppm). After 42 minutes, the NCO-content had dropped to 30.45%. No further change was observed after an additional 10 minutes at 200° C. The product was then quench cooled to 50° C. The material was allowed to stand for 5 days at 25° C., after which it was still liquid, having an NCO-content of 29.2%.

EXAMPLE 2

Example 1 was repeated using 1506 parts of 4,4'-diisocyanatodiphenylmethane, 0.0556 parts of the 3% phospholine oxide solution (1 ppm), a reaction temperature of 198° C., and a reaction time of 40 minutes. The material was quench cooled to 50° C. The resultant liquid had an NCO-content of 26.6%. After ageing at 25° C. for 5 days, the NCO-content of the liquid was 25.9%.

EXAMPLE 3

Using the same equipment as in Example 1, one ppm of phospholine oxide was added to 4,4'-diisocyanatodiphenylmethane at 50° C. Within 30 minutes, the reaction mixture was heated to 200° C. and held at that temperature for 14 minutes. After quench cooling to 50° C. and standing overnight, the product had an NCO-content of 26.5%. After ageing for 5 days at 25° C., the NCO-content of the liquid was stable at 26.1%.

EXAMPLE 4

260 pounds of 4,4'-diisocyanatodiphenylmethane were heated in a 50 gal. stainless steel reactor to 197° C. At this temperature, 0.8 grams of a 3% phospholine oxide solution in toluene (0.2 ppm) was added. After 43 minutes, an additional 0.8 grams of the phospholine oxide solution was added. After 75 minutes, the reaction was quench cooled to 80° C. resulting in a product with an NCO-content of 29.8%.

EXAMPLE 5

Example 1 was repeated using 482 parts of 4,4'-diisocyanatodiphenylmethane, 0.0085 parts of the 3% phospholine oxide solution (0.5 ppm), a reaction temperature of 180° C., and a reaction time of 60 minutes. The material was quench cooled to 50° C. The resultant liquid had an NCO-content of 28.9%. After ageing at 25° C. for 5 days, the NCO-content of the liquid was 27.1%.

EXAMPLE 6

Example 1 was repeated using 481 parts of 4,4'-diisocyanatodiphenylmethane, 0.0088 parts of the 3% phospholine oxide solution (0.5 ppm), a reaction temperature of 190° C., and a reaction time of 57 minutes. The material was quenched cooled to 50° C. The resultant liquid had an NCO-content of 28.7%. After ageing at 25° C. for 5 days, the NCO-content of the liquid was 26.8%.

EXAMPLE 7

Example 1 was repeated using 505 parts of 4,4'-diisocyanatodiphenylmethane, 0.0090 parts of the 3% phospholine oxide solution (0.5 ppm), a reaction temperature of 200° C., and a reaction time of 56 minutes. The material was quench cooled to 50° C. The resultant liquid had an NCO-content of 28.4%. After ageing at 25° C. for 5 days, the NCO-content of the liquid was 26.5%.

EXAMPLE 8

Example 1 was repeated using 501 parts of 4,4'-diisocyanatodiphenylmethane, 0.0084 parts of the 3% phospholine oxide solution (0.5 ppm), a reaction temperature of 210° C., and a reaction time of 54 minutes. The material was quench cooled to 50° C. The resultant liquid had an NCO-content of 28.1%. After ageing at 25° C. for 5 days, the NCO-content of the liquid was 26.5%.

EXAMPLE 9

Example 1 was repeated using 420 parts of 4,4'-diisocyanatodiphenylmethane, 0.0135 parts of the 3% phospholine oxide solution (1.0 ppm), a reaction temperature of 180° C., and a reaction time of 71 minutes. The material was quench cooled to 50° C. The resultant liquid had an NCO-content of 23.3%. After ageing at 25° C. for 5 days, the NCO-content of the liquid was 20.5%.

EXAMPLE 10

Example 1 was repeated using 452 parts of 4,4'-disocyanatodiphenylmethane, 0.0160 parts of the 3% phospholine oxide solution (1.0 ppm), a reaction temperature of 190° C., and a reaction time of 62 minutes. The material was quench cooled to 50° C. The resultant liquid had an NCO-content of 23.2%. After ageing at 25° C. for 5 days, the NCO-content of the liquid was 20.3%.

EXAMPLE 11

Example 1 was repeated using 547 parts of 4,4'-diisocyanatodiphenylmethane, 0.0188 parts of the 3% phospholine oxide solution (1.0 ppm), a reaction temperature of 200° C., and a reaction time of 32 minutes. The material was quench cooled to 50° C. The resultant liquid had an NCO-content of 23.3%. After ageing at 25° C. for 5 days, the NCO-content of the liquid was 20.5%.

EXAMPLE 12

Example 1 was repeated using 498 parts of 4,4'-diisocyanatodiphenylmethane, 0.0166 parts of the 3% phospholine oxide solution (1.0 ppm), a reaction temperature of 210° C., and a reaction time of 29 minutes. The material was quench cooled to 50° C. The resultant liquid had an NCO-content of 23.1%. After ageing at 25° C. for 5 days, the NCO-content of the liquid was 20.1%.

EXAMPLE 13

Example 1 was repeated using 493 parts of 4,4'-diisocyanatodiphenylmethane, 0.0320 parts of the 3% phospholine oxide solution (2.0 ppm), a reaction temperature of 180° C., and a reaction time of 20 minutes. The material was quench cooled to 50° C. The resultant liquid had an NCO-content of 23.4%. After ageing at 25° C. for 5 days, the NCO-content of the liquid was 20.7%.

EXAMPLE 14

Example 1 was repeated using 469 parts of 4,4'-diisocyanatodiphenylmethane, 0.0320 parts of the 3% phospholine oxide solution (2.0 ppm), a reaction temperature of 190° C., and a reaction time of 19 minutes. The material was quench cooled to 50° C. The resultant liquid had an NCO-content of 23.3%. After ageing at 25° C. for 5 days, the NCO-content of the liquid was 20.5%.

EXAMPLE 15

Example 1 was repeated using 502 parts of 4,4'-diisocyanatodiphenylmethane, 0.0390 parts of the 3% phospholine oxide solution (2.0 ppm), a reaction temperature of 200° C., and a reaction time of 17 minutes. The material was quench cooled to 50° C. The resultant liquid had an NCO-content of 23.3%. After ageing at 25° C. for 5 days, the NCO-content of the liquid was 20.5%.

EXAMPLE 16

Example 1 was repeated using 470 parts of 4,4'-diisocyanatodiphenylmethane, 0.0313 parts of the 3% phospholine oxide solution (2.0 ppm), a reaction temperature of 210° C., and a reaction time of 15 minutes. The material was quench cooled to 50° C. The resultant liquid had an NCO-content of 23.3%. After ageing at 25° C. for 5 days, the NCO-content of the liquid was 20.5%.

EXAMPLE 17

348 lbs. of 4,4'-diisocyanatodiphenylmethane were heated in a 50 gal. stainless steel reactor to 194° C. At this temperature, 1.58 grams of a 3% phospholine oxide solution in toluene (0.3 ppm) was added. After 35 minutes, an additional 1.58 grams of the phospholine oxide solution was added. After 84 minutes, the reaction was quench cooled to 80° C. resulting in a product with an NCO-content of 26.3%.

EXAMPLE 18

A continuous experiment was run by pumping 4,4'-diisocyanatodiphenylmethane containing 1.0 ppm (by weight) of phospholine oxide into a reactor at 200° C. at such a flow rate to give a 2 hour residence time in the reactor. After steady state conditions were attained, the material leaving the reactor was observed to have an NCO value of 27.5%.

EXAMPLE 19

A continuous experiment was run by pumping 4,4'-diisocyanatodiphenylmethane containing 0.5 ppm (by weight) of phospholine oxide into a reactor at 200° C. at such a flow rate to give a 2 hour residence time in the reactor. After steady state conditions were attained, the material leaving the reactor was found to have an NCO content of 30.8%.

What is claimed is:

1. A process for producing a liquid, storage stable, partially carbodiimidized methylene bis(phenylisocyanate) comprising:

(A) heating methylene bis(phenylisocyanate) to a temperature of from 150° C. to 300° C. in the presence of from 1 ppb to 10 ppm of a phospholene oxide of the formula:

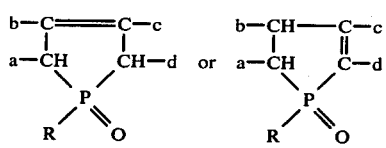

wherein

R represents a lower alkyl radical, a phenyl radical, an alkoxy radical, a hydrogen atom or an alkenyl radical;

a, b, c, and d each represent hydrogen, a halogen atom, a lower alkyl, a lower alkenyl, phenyl, a cyclohexyl, or a polymethylene group which together with two neighboring carbon atoms of the heterocyclic ring forms a cycloaliphatic ring, and, (B) cooling the reaction mixture to 100° C. or less once the desired isocyanate content is reached.

2. The process of claim 1, wherein said phospholine oxide is an isomer mixture of 1-methyl-1-oxophospholine.

3. The process of claim 1 wherein the reaction mixture is heated to from 180° C. to 240° C.

4. The process of claim 3 wherein the reaction mixture is heated to from 190° to 210° C.

5. The process of claim 1 wherein said phospholine oxide is used in an amount of from 0.05 ppm to 5 ppm.

6. The process of claim 1 wherein step (B), comprises cooling to from 20° to 60° C.

* * * * *